(12) United States Patent
Crooke et al.

(10) Patent No.: US 6,376,661 B1
(45) Date of Patent: Apr. 23, 2002

(54) HUMAN RNASE H AND COMPOSITIONS AND USES THEREOF

(75) Inventors: Stanley T. Crooke, Carlsbad; Walter F. Lima, San Diego; Hongjiang Wu, Carlsbad, all of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/684,254

(22) Filed: Oct. 6, 2000

Related U.S. Application Data

(63) Continuation of application No. 09/343,809, filed on Jun. 30, 1999, now abandoned, which is a continuation of application No. 09/203,716, filed on Dec. 2, 1998, now Pat. No. 6,001,653.
(60) Provisional application No. 60/067,458, filed on Dec. 4, 1997.

(51) Int. Cl.[7] .............................................. C07H 21/04

(52) U.S. Cl. .................................. 536/24.31; 536/23.1

(58) Field of Search .............................. 536/24.31, 23.1

(56) References Cited

FOREIGN PATENT DOCUMENTS

| JP | 05038286 | * | 2/1993 |
| WO | WO-9506718 | * | 9/1994 |

OTHER PUBLICATIONS

Jean–Laurent Casanova et al., T Cell Receptor Genes in a Series of Class I Major Histocompatibility Complex–restricted Cytotoxic T Lymphocyte Clones Specific for a Plasmodium berghei Nonapeptide: Implications for T cell Allelic Exclusion and Antigen–specific Repertoire, J. Exp. Med. vol. 174 pp. 1371–1383, 1991.*
Wolfgang Holtmeir et al., The o T Cell Receptor Repertoire in Human Colon and Peripheral Blood Is Oligoclonal Irrespective of V Region usage, The American Society for Clinical Investigation, Inc. vol. 96, pp. 1108–1117, 1995.*
Busen et al., "Ribonuclease H Levels during the Response of Bovine Lymphocytes to Concanavalin A", Eur. J. Biochem., 1977, 74, 203–208.
Busen, W., and Hausen, P., "Distinct Ribonuclease H Activities in Calf Thymus", Bur. J. Biochem., 1975, 52, 179–190.
Busen, W., J. Biol. Chem., "The Subunit Structure of Calf Thymus Ribonuclease HI As Revealed by Immunological Analysis", 1982, 257, 7106–7108.
Cazenave et al., "Comparative inhibition of rabbit globin mRNA translation by modified antisense oligodeoxynucleotides", Nucleic Acid Res., 1989, 17, 4255–4273.
Crooke, S.T. et al., "Kinetic characteristics of Escherichia coli Rnase H1: cleavage of various antisense oligonucleotide–RNA duplexes", Biochem. J., 1995, 312, 599–608.

Dash et al., "Selective elimination of mRNAs in vivo: Complementary oligodeoxynucleotides promote RNA degradation by an Rnase H–like activity", Proc. Nat'l Acad. Sci. USA, 1987, 84, 7896–7900.
Frank et al., "Purification and characterization of human ribonuclease HII", Nucleic Acids Res., 1994, 22, 5247–5254.
Gagnor et al., "α–DNA VI:comparative study of α–and β–anomeric oligodeoxyribonucleotides in hybridization to mRNA and in cell free translation inhibition", Nucleic Acid Res., 1987, 15, 10419–10436.
Itaya, M., "Isolation and characterization of a second Rnase H (Rnase HII) of Escherichia coli K–12 encoded by the rnhB gene", Proc. Natl. Acad. Sci. USA, 1990, 87, 8587–8591.
Itaya, M. and Kondo K., Molecular cloning of a ribonuclease H (Rnase HI) gene from an extreme thermophile Thermus thermophilus HB8: a thermostable Rnase H can functionally replace the Escherichia coli enzyme in vivo.
Itaya et al., "Selective cloning of genes encoding Rnase H from Salmonella typhimurium, Saccharomyces cerevisiae and Escherichia coli rnh mutant", Mol. Gen. Genet., 1991, 227, 438–445.
Kanaya et al., Importance of the Positive Charge Cluster in Escherichia coli Ribonuclease HI for the Effective Binding of the S J. Biol. Chem., 1991, 266, 11621–11627.
Kane, C. M., "Renaturase and Ribonuclease H: A Novel Mechanism That Influences Transcript Displacement by RNA Polymerase II in Vitro", Biochemistry, 1988, 27, 3187–3196.
Katayanagi et al., "Crystal Structure of Escherichia coli Rnase HI in Complex with $Mg^{2+}$ at 2.8 A Resolution: Proof for a Single $Mg^2$ Binding Site", Proteins: Struct., Funct., Genet., 1993, 17, 337–346.
Katayanagi et al., "Three–dimensional structure of ribonuclease H from E. Coli", Nature, 1990, 347, 306–309.
Lima, W.F. and Crooke, S.T., "Binding Affinity and Specificity of Escherichia coli Rnase H1: Impact on the Kinetics of Catalysis of Antisense Oligonucleotide–RNA Hybrids", Biochemistry, 1997, 36, 390–398.
Lima, W.F. et al., "The Influence of Antisense Oligonucleotide–induced RNA Structure on Escherichia coli Rnase H1 Activity", J. Biol. Chem., 1997, 272, 18191–18199.
Monia et al., "Evaluation of 2'–Modified Oligonucleotides Containing 2'–Deoxy Gaps as Antisense Inhibitors of Gene Expression", J. Biol. Chem., 1993, 266:13, 14514–14522.
Nakamura et al., "How does Rnase H recognize a DNA–RNA hybrid", Proc. Natl. Acad. Sci. USA, 1991, 88, 11535–11539.

(List continued on next page.)

Primary Examiner—Andrew Wang
(74) Attorney, Agent, or Firm—Licata & Tyrrell P.C.

(57) ABSTRACT

The present invention provides polynucleotides and polypeptides encoded thereby of human Type 2 RNase H. Methods of using these polynucleotides and polypeptides in enhancing antisense oligonucleotide therapies are also provided.

1 Claim, 1 Drawing Sheet

OTHER PUBLICATIONS

Tidd, D.M. and Worenius, H.M., "Partial protection of oncogene, anti–sense oligodeoxynucleotides against serum nuclease degradation using terminal methylphosphonate groups", *Br. J. Cancer*, 1989, 60, 343 ups.

Tidd, D.M. et al., "Evaluation of N–ras oncogene anti–sense, sense and nonsense sequence methylphosphonate oligonucleotide analogues", *Anti–Cancer Drug Des.*, 1988, 3, 117.

Walder, R.Y. and Walder, J.A., "Role of Rnase H in hybrid–arrested translation by antisense oligonucleotides", *Proc. Nat'l Acad. Sci. USA,* 1988, 85, 5011–5015.

Wintersberger, U., "Ribonucleases H of Retroviral and Cellular Origin", *Pharmac. Ther.,* 1990, 48, 259–280.

Yang et al., "Structure of Ribonuclease H Phased at 2 A Resolution by MAD Analysis of Selenomethionyl Protein", Science, 1990, 249, 1398–1405.

Agrawal, S. et al., "Site–specific excision from RNA by Rnase H and mixed–phosphate–backbone oligodeoxynucleotides" *Proc. Natl. Acad. Sci. USA* 1990 87(4):1401–1405.

Boado R.J. et al., "Complete inactivation of target mRNA by Biotinylated antisense oligodeoxynucleotide–avidin conjugates" *Bioconjug. Chem.* 1994 5(5):406–410.

Bordier, B. et al., "Sequence–specific Inhibition of Human Immunodeficiency Virus (HIV) reverse transcription by Antisense Oligonucleotides:Comparative Study in Cell–free assays and in HIV–infected cells", *Proc. Natl. Acad. Sci. USA* 1995 92:9383–9387.

Chiang, M.Y. et al., "Antisense oligonucleotides inhibit intercellular adhesion molecule 1 expression by two distinct mechanisms", *J. Biol. Chem.* 1991 266(27):18162–18171.

Dean, N.M. et al., "Inhibition of protein kinase C–alpha expression in human A549 cells by antisense oligonucleotides inhibits induction of intercellular adhesion molecule 1 (CAM–1) mRNA by phorbol esters" *J. Biol. Chem.* 1994 269(23):16416–16424.

Furdon, P.J. et al., "RNASE H cleavage of RNA hybridized to oligonucleotides containing methylphosphonate, phosphorothioate and phosphodiester bonds", *Nucleic Acids Res.* 1989 17(22):9193–9204.

Ghosh, M.K. et al., "Phosphorothioate–phosphodiester oligonucleotide copolymers; assessment for antisense application", *Anticancer Drug Des.* 1993 8(1):15–32.

Giles R.V. et al., "Enhanced RNase H activity with methylphosphonodiester/phosphodiester chimeric antisense oligodeoxynucleotides", *Anticancer Drug Des.* 1992 7(1):37–48.

Giles, R.V. et al., "Increased specificity for antisense oligodeoxynucleotide targeting of RNA cleavage by RNase H using chimeric methylphosphonodiester/phosphodiester structures", *Nucleic Acids Res.* 1992 20(4):763–770.

Godard, G. et al., "Antisense effects of cholesterol–oligonucleotide conjugates associated with poly(alkylcyanoacrylate) nonoparticles", *Eur. J. Biochem.* 1995 232(2):404–410.

Gottikh, M. et al., "Alpha beta chimeric antisense oligonucleotides; synthesis and nuclease resistance in biological media", *Antisense Res. Dev.* 1994 4(4):251–258.

Hoke, G.D. et al., "Effects of phosphorothioate capping on antisense oligonucleotide stability, hybridization and antiviral efficacy versus herpes simplex virus infection", *Nucleic Acids Res.* 1991 19(20)5743–5748.

Lee C.H. et al., "Antisense gene suppression against human ICAM–1, ELAM–1 and VCAM–1 in cultured human umbilical vein endothelial cells", *Shock* 1995 4(1):1–10.

Liu P.K. et al., "Suppression of ischemia–induced fos expression and AP–1 activity by an antisense oligodeoxynucleotide to c–fos mRNA", *Ann. Neurol.* 1994 36(4):566–576.

Rosolen A. et al., "Effect of over–expression of bacterial ribonuclease H on the utility of antisense MYC oligodeoxynucleotides in the monocytic leukemia cell line U937", *Biochimie* 1993 75(1–2):79–87.

Saison–Behmoaras B.T. et al. "Short modified antisense oligonucleotides directed against Ha–ras point mutation induce selective cleavage of the mRNA and inhibit T24 cells proliferation", *EMBO J.* 1991 10(5):1111–1118.

Dagle J.M. et al., "Targeted degradation of mRNA in Xenopus oocytes and embryos directed by modified oligonucleotides: studies of An2 and cyclin in embryogenesis", *Nucleic Acids Res.* 1990 18(16):4751–4757.

Kawasaki E., "Quantitative hybridization–arrest of mRNA in Xenopus oocytes using single–stranded complementary DNA or oligonucleotide probes", *Nucleic Acids Res. 1985 13(13):4991–5005.*

Quartin R.S., "Number and distribution of methylphosphonate linkages in oligodeoxynucleotides affect exo–and endonuclease sensitivity and ability to form RNASE H substrates", *Nucleic Acids Res.* 1989 17(18):7253–7262.

* cited by examiner

```
Human      MSWLLFLAHRVALAAALPCRRGSRGFGMFYAVRRGRKTGVFLITWNECRAQVDRFPAARFKKFATEDEAWAFVRKSAS
Chicken    MLRWL-----VAL-LSHSCFVSKGGGMFYAVRRGMFYAVRKGRQTGVYRTWAECQQQVNRFPSASFKKFATEKEAWAFVGAGPP
Yeast                               MARQGNFYAVRKGRETGIYNTWNECKNQVDGYGGAIYKKFNSYEQAKSFLGQPNT
Mouse EST                               GICGLGMFYAVRRGRRPGVFLSWSECKAQVDRFPAARFKKFATEDEAWAFVRSSSS Human      PEVSEGHENQHGQESEAKPGKRLREPLDGDG-------------------------------
Chicken    DGQQSAPAETHGASAVAQENASHREEPETDV-------------------------------
Yeast      TSNYGSSTHAGGQVSKPHTTQKRVHRRNRPLHYSSLTSSACSSLSSANTNTFYSVKSNVPNIESKIFNNWKDCQA
Mouse EST  PDGSKGQESAHEQKSQAKTSKRPREPL
                                          @@

Human      ------------HESAQPYAKHMKPSVEP-APPVSRDTFSYMGDFVVVYTDGCCSSNGRRKPRA
Chicken    ---------LCCNACKRPYEQSTNEEHTVRRAKH---DEEQSTPVVSEAKFSYMGEFAVVYTDGCCSGNGRNRARA
Yeast      YVKHKRGITFKKFEDQLAAENFISGMSAHDY-KLMNISKESFESKYKLSSNTMYNKSMNVYCDGSSFGNGTSSSRA
E.coli                                            MLKQVEIFTDGSCLGNPGPGGYG
Mouse EST                                            VVVYTDGCCSSNGRKRARA
                                        @                    **

Human      GIGVYWGPGHPLNVGI-RLPGRQTNQRAEIHAACKAIEQAKTQNIN-----KLVLYTDSMFTINGITNWVQGWKKN
Chicken    GIGVYWGPGHPLNISE-RLPGRQTNQRAEIHAACKAIEQAKSQNIK-----KLIIYTDSKFTINGITSWVENWKTN
Yeast      GYGAYFEGAPEENISEPLLSGAQTNNRAEIEAVSEALKKIWEKLTNEKEKVNYQIKTDSEYVTKLLNDRYMTYDNK
E.coli     AILRYRGREKTFSAGY---TRTTNNRMELMAAIVALEALKEHC------EVILSTDSQYVRQGITQWIHNWKRR
Mouse EST  GIGVYWGPGHPLNVRI-RLPGRQTNQRAEIHAACKAVMQAKAQNIS-----KLVLYTDSMFTINGITNWVQGWKKN
                *                                                    *

Human      GWKTSAGKEVINKEDFVALERL--------TQGMDIQWMHVPGHSGFIGNEEADRLAREGA-KQSED
Chicken    GWRTSSGGSVINKEDFQKLDSL--------SKGIEIQWMHIPGHAGFQGNEEADRLAREGASKQKL
Yeast      KLEGLPNSDLIVPLVQRFVKVKKYYELNKECFKNNGKFQIEWVKGHDGDPGNEMADFLAKKGASRR
E.coli     GWKTADKKPVKNVDLWQRLDAA--------LGQHQIKWEWVKGHAGHPENERCDELARAAAMNPTLEDTGYQVEV
Mouse EST  GWRTSTGKDVINKEDFMELDEL--------TQGMDIQWMHIPGHSGFVGNEE
```

FIG. 1

HUMAN RNASE H AND COMPOSITIONS AND USES THEREOF

This application is a continuation of U.S. Ser. No. 09/343,809, filed Jun. 30, 1999, now abandoned which is a continuation of U.S. Ser. No. 09/203,716, filed Dec. 2, 1998 and issued as U.S. Pat. No. 6,001,653 on Dec. 14, 1999 which claims the benefit of priority of U.S. Provisional Application Ser. No. 60/067,458, filed Dec. 4, 1997.

FIELD OF THE INVENTION

The present invention relates to a human Type 2 RNase H which has now been cloned, expressed and purified to electrophoretic homogeneity and human RNase H and compositions and uses thereof.

BACKGROUND OF THE INVENTION

RNase H hydrolyzes RNA in RNA-DNA hybrids. This enzyme was first identified in calf thymus but has subsequently been described in a variety of organisms (Stein, H. and Hausen, P., *Science,* 1969, 166, 393–395; Hausen, P. and Stein, H.,*Eur. J. Biochem.,* 1970, 14, 278–283). RNase H activity appears to be ubiquitous in eukaryotes and bacteria (Itaya, M. and Kondo K. *Nucleic Acids Res.,* 1991, 19, 4443–4449; Itaya et al., *Mol. Gen. Genet.,* 1991 227, 438–445; Kanaya, S., and Itaya, M., *J. Biol. Chem.,* 1992, 267, 10184–10192; Busen, W., *J. Biol. Chem.,* 1980, 255, 9434–9443; Rong, Y. W. and Carl, P. L., 1990, *Biochemistry* 29, 383–389; Eder et al., *Biochimie,* 1993 75, 123–126). Although RNase Hs constitute a family of proteins of varying molecular weight, nucleolytic activity and substrate requirements appear to be similar for the various isotypes. For example, all RNase Hs studied to date function as endonucleases, exhibiting limited sequence specificity and requiring divalent cations (e.g., $Mg^{2+}$, $Mn^{2+}$) to produce cleavage products with 5' phosphate and 3' hydroxyl termini (Crouch, R. J., and Dirksen, M. L., *Nuclease,* Linn, S, M., & Roberts, R. J., Eds., Cold Spring Harbor Laboratory Press, Plainview, N.Y. 1982, 211–241).

In addition to playing a natural role in DNA replication, RNase H has also been shown to be capable of cleaving the RNA component of certain oligonucleotide-RNA duplexes. While many mechanisms have been proposed for oligonucleotide mediated destabilization of target RNAs, the primary mechanism by which antisense oligonucleotides are believed to cause a reduction in target RNA levels is through this RNase H action. Monia et al., *J. Biol. Chem.,* 1993, 266:13, 14514–14522. In vitro assays have demonstrated that oligonucleotides that are not substrates for RNase H can inhibit protein translation (Blake et al., *Biochemistry,* 1985, 24, 6139–4145) and that oligonucleotides inhibit protein translation in rabbit reticulocyte extracts that exhibit low RNase H activity. However, more efficient inhibition was found in systems that supported RNase H activity (Walder, R. Y. and Walder, J. A.,*Proc. Nat'l Acad. Sci. USA,* 1988, 85, 5011–5015; Gagnor et al., *Nucleic Acid Res.,* 1987, 15, 10419–10436; Cazenave et al., *Nucleic Acid Res.,* 1989, 17, 4255–4273; and Dash et al., *Proc. Nat'l Acad. Sci. USA,* 1987, 84, 7896–7900.

Oligonucleotides commonly described as "antisense oligonucleotides" comprise nucleotide sequences sufficient in identity and number to effect specific hybridization with a particular nucleic acid. This nucleic acid or the protein(s) it encodes is generally referred to as the "target." Oligonucleotides are generally designed to bind either directly to mRNA transcribed from, or to a selected DNA portion of, a preselected gene target, thereby modulating the amount of protein translated from the mRNA or the amount of mRNA transcribed from the gene, respectively. Antisense oligonucleotides may be used as research tools, diagnostic aids, and therapeutic agents.

"Targeting" an oligonucleotide to the associated nucleic acid, in the context of this invention, also refers to a multistep process which usually begins with the identification of the nucleic acid sequence whose function is to be modulated. This may be, for example, a cellular gene (or mRNA transcribed from the gene) whose expression is associated with a particular disorder or disease state, or a foreign nucleic acid from an infectious agent. The targeting process also includes determination of a site or sites within this gene for the oligonucleotide interaction to occur such that the desired effect, either detection or modulation of expression of the protein, will result.

RNase HI from *E.coli* is the best-characterized member of the RNase H family. The 3-dimensional structure of *E.coli* RNase HI has been determined by x-ray crystallography, and the key amino acids involved in binding and catalysis have been identified by site-directed mutagenesis (Nakamura et al., *Proc. Natl. Acad. Sci. USA,* 1991, 88, 11535–11539; Katayanagi et al., *Nature,* 1990, 347, 306–309; Yang et al., *Science,* 1990, 249, 1398–1405; Kanaya et al., *J. Biol. Chem.,* 1991, 266, 11621–11627). The enzyme has two distinct structural domains. The major domain consists of four α helices and one large β sheet composed of three antiparallel β strands. The $Mg^{2+}$ binding site is located on the β sheet and consists of three amino acids, Asp-10, Glu-48, and Gly-11 (Katayanagi et al., *Proteins: Struct., Funct., Genet.,* 1993, 17, 337–346). This structural motif of the $Mg^{2+}$ binding site surrounded by β strands is similar to that in DNase I (Suck, D., and Oefner, C.,*Nature,* 1986, 321, 620–625). The minor domain is believed to constitute the predominant binding region of the enzyme and is composed of an α helix terminating with a loop. The loop region is composed of a cluster of positively charged amino acids that are believed to bind electrostatistically to the minor groove of the DNA/RNA heteroduplex substrate. Although the conformation of the RNA/DNA substrate can vary, from A-form to B-form depending on the sequence composition, in general RNA/DNA heteroduplexes adopt an A-like geometry (Pardi et al., *Biochemistry,* 1981, 20, 3986–3996; Hall, K. B., and Mclaughlin, L. W., *Biochemistry,* 1991, 30, 10606–10613; Lane et al., *Eur. J. Biochem.,* 1993, 215, 297–306). The entire binding interaction appears to comprise a single helical turn of the substrate duplex. Recently the binding characteristics, substrate requirements, cleavage products and effects of various chemical modifications of the substrates on the kinetic characteristics of *E.coli* RNase HI have been studied in more detail (Crooke, S. T. et al., *Biochem. J.,* 1995, 312, 599–608; Lima, W. F. and Crooke, S. T., *Biochemistry,* 1997, 36, 390–398; Lima, W. F. et al., *J. Biol. Chem.,* 1997, 272, 18191–18199; Tidd, D. M. and Worenius, H. M., *Br. J. Cancer,* 1989, 60, 343; Tidd, D. M. et al., *Anti-Cancer Drug Des.,* 1988, 3, 117.

In addition to RNase HI, a second *E.coli* RNase H, RNase HII has been cloned and characterized (Itaya, M.,*Proc. Natl. Acad. Sci. USA,* 1990, 87, 8587–8591). It is comprised of 213 amino acids while RNase HI is 155 amino acids long. *E. coli* RNase HIM displays only 17% homology with *E.coli* RNase HI. An RNase H cloned from *S. typhimurium* differed from *E.coli* RNase HI in only 11 positions and was 155 amino acids in length (Itaya, M. and Kondo K., *Nucleic Acids Res.,* 1991, 19, 4443–4449; Itaya et al., *Mol. Gen. Genet.,* 1991, 227, 438–445). An enzyme cloned from *S.* cerevisae was 30% homologous to E.coli RNase HI (Itaya, M. and Kondo K., *Nucleic Acids Res.,* 1991, 19, 4443–4449; Itaya et al., *Mol. Gen. Genet.,* 1991, 227, 438–445). Thus, to date, no enzyme cloned from a species other than *E. coli* has displayed substantial homology to *E.coli* RNase H II.

Proteins that display RNase H activity have also been cloned and purified from a number of viruses, other bacteria and yeast (Wintersberger, *U. Pharmac. Ther.,* 1990, 48, 259–280). In many cases, proteins with RNase H activity appear to be fusion proteins in which RNase H is fused to the amino or carboxy end of another enzyme, often a DNA or RNA polymerase. The RNase H domain has been consistently found to be highly homologous to *E.coli* RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., *Eur. J. Biochem.,* 1977, 74, 203–208). RNase H Type 1 enzymes are reported to have molecular weights in the 68–90 kDa range, be activated by either $Mn^{2+}$ or $Mg^{2+}$ and be insensitive to sulfhydryl agents. In contrast, RNase H Type 2 enzymes have been reported to have molecular weights ranging from 31–45 kDa, to require $Mg^{2+}$ to be highly sensitive to sulfhydryl agents and to be inhibited by $Mn^{2+}$ (Busen, W., and Hausen, P., *Eur. J. Biochem.,* 1975, 52, 179–190; Kane, C. M., *Biochemistry,* 1988, 27, 3187–3196; Busen, W., *J. Biol. Chem.,* 1982, 257, 7106–7108.).

An enzyme with Type 2 RNase H characteristics has been purified to near homogeneity from human placenta (Frank et al., *Nucleic Acids Res.,* 1994, 22, 5247–5254). This protein has a molecular weight of approximately 33 kDa and is active in a pH range of 6.5–10, with a pH optimum of 8.5–9. The enzyme requires $Mg^{2+}$ and is inhibited by $Mn^{2+}$ and n-ethyl maleimide. The products of cleavage reactions have 3' hydroxyl and 5' phosphate termini.

Despite the substantial information about members of the RNase family and the cloning of a number of viral, prokaryotic and yeast genes with RNase H activity, until now, no mammalian RNase H had been cloned. This has hampered efforts to understand the structure of the enzyme(s), their distribution and the functions they may serve.

In the present invention, a cDNA of human RNase H with Type 2 characteristics and the protein expressed thereby are provided.

SUMMARY OF THE INVENTION

The present invention provides polypeptides which have been identified as novel human Type 2 RNase H by homology between the amino acid sequence set forth in FIG. 1 and known amino acid sequences of chicken, yeast and *E. coli* RNase H1 as well as an EST deduced mouse RNase H homolog. In accordance with this aspect of the present invention, as a preferred embodiment, a sample of *E. coli* DH5α containing a BLUESCRIPT® plasmid containing a human cDNA nucleic acid molecule encoding a human Type 2 RNase H polypeptide deposited as ATCC Deposit No. ATCC 98536.

The present invention also provides polynucleotides that encode human Type 2 RNase H, vectors comprising nucleic acids encoding human RNase H, host cells containing such vectors, antibodies targeted to human Type 2 RNase H, human Type 2 RNase H--his-tag fusion peptides, nucleic acid probes capable of hybridizing to a nucleic acid encoding a human RNase H polypeptide. Pharmaceutical compositions which include a human Type 2 RNase H polypeptide or a vector encoding a human Type 2 RNase H polypeptide are also provided. These compositions may additionally contain an antisense oligonucleotide.

The present invention is also directed to methods of enhancing antisense inhibition of expression of a target protein via use of human Type 2 RNase H. Methods of screening for effective antisense oligonucleotides and of producing effective antisense oligonucleotides using human Type 2 RNase H are also provided.

Yet another object of the present invention is to provide methods for identifying agents which modulate activity and/or levels of human Type 2 RNase H. In accordance with this aspect, the polynucleotides and polypeptides of the present invention are useful for research, biological and clinical purposes. For example, the polynucleotides and polypeptides are useful in defining the interaction of human Type 2 RNase H and antisense oligonucleotides and identifying means for enhancing this interaction so that antisense oligonucleotides are more effective at inhibiting their target mRNA.

Yet another object of the present invention is to provide a method of prognosticating efficacy of antisense therapy of a selected disease which comprises measuring the level or activity of human RNase H in a target cell of the antisense therapy. Similarly, oligonucleotides can be screened to identify those oligonucleotides which are effective antisense agents by measuring binding of the oligonucleotide to the human Type 2 RNase H.

BRIEF DESCRIPTION OF THE DRAWINGS

FIG. 1 provides a human Type 2 RNase H primary sequence (286 amino acids; SEQ ID NO: 1) and sequence comparisons with chicken (293 amino acids; SEQ ID NO: 2), yeast (348 amino acids; SEQ ID NO: 3) and *E. coli* RNase H1 (155 amino acids; SEQ ID NO: 4) as well as an EST deduced mouse RNase H homolog (GenBank accession no. AA389926 and AA518920; SEQ ID NO: 5). Boldface type indicates amino acid residues identical to human. "@" indicates the conserved amino acid residues implicated in *E. coli* RNase H1 $Mg^{2+}$ binding site and catalytic center (Asp-10, Gly-11, Glu-48 and Asp-70). "*" indicates the conserved residues implicated in *E. coli* RNases H1 for substrate binding.

DETAILED DESCRIPTION OF THE INVENTION

A Type 2 human RNase H has now been cloned and expressed. The enzyme encoded by this cDNA is inactive against single-stranded RNA, single-stranded DNA and double-stranded DNA. However, this enzyme cleaves the RNA in an RNA/DNA duplex and cleaves the RNA in a duplex comprised of RNA and a chimeric oligonucleotide with 2' methoxy flanks and a 5-deoxynucleotide center gap. The rate of cleavage of the RNA duplexed with this so-called "deoxy gapmer" was significantly slower than observed with the full RNA/DNA duplex. These properties are consistent with those reported for *E.coli* RNase H1 (Crooke et al., *Biochem. J.,* 1995, 312, 599–608; Lima, W. F. and Crooke, S. T., *Biochemistry,* 1997, 36, 390–398). They are also consistent with the properties of a human Type 2 RNase H protein purified from placenta, as the molecular weight (32 kDa) is similar to that reported by Frank et al., *Nucleic Acids Res.,* 1994, 22, 5247–5254) and the enzyme is inhibited by $Mn^{2+}$. Accordingly, we refer to the newly cloned human RNase H as Type 2 RNase H or human RNase H1.

Thus, in accordance with one aspect of the present invention, there are provided isolated polynucleotides which encode human Type 2 RNase H polypeptides. By "polynucleotides" it is meant to include any form of RNA or DNA such as mRNA or cDNA or genomic DNA, respectively, obtained by cloning or produced synthetically by well known chemical techniques. DNA may be double- or single-stranded. Single-stranded DNA may comprise the coding or sense strand or the non-coding or antisense strand.

Methods of isolating a polynucleotide of the present invention via cloning techniques are well known. For example, to obtain the cDNA contained in ATCC Deposit No. 98536, primers based on a search of the XREF database were used. An approximately 1 Kb cDNA corresponding to the carboxy terminal portion of the protein was cloned by 3' RACE. Seven positive clones were isolated by screening a liver cDNA library with this 1 Kb cDNA. The two longest clones were 1698 and 1168 base pairs. They share the same 5' untranslated region and protein coding sequence but differ in the length of the 3' UTR. A single reading frame encoding a 286 amino acid protein (calculated mass: 32029.04 Da) was identified (FIG. 1). The proposed initiation codon is in agreement with the mammalian translation initiation consensus sequence described by Kozak, M., *J. Cell Biol.*, 1989, 108, 229–241, and is preceded by an in-frame stop codon. Efforts to clone cDNA's with longer 5' UTR's from both human liver and lymphocyte cDNA's by 5' RACE failed, indicating that the 1698-base-pair clone was full length.

In a preferred embodiment, the polynucleotide of the present invention comprises the nucleic acid sequence of the cDNA contained within ATCC Deposit No. 98536. The deposit of *E. coli* DH5α containing a BLUESCRIPT® plasmid containing a human Type 2 RNase H cDNA was made with the American Type Culture Collection, 12301 Park Lawn Drive, Rockville, Md. 20852, USA, on Sep. 4, 1997 and assigned ATCC Deposit No. 98536. The deposited material is a culture of *E. coli* DH5α containing a BLUESCRIPT® plasmid (Stratagene, La Jolla Calif.) that contains the full-length human Type 2 RNase H cDNA. The deposit has been made under the terms of the Budapest Treaty on the international recognition of the deposit of micro-organisms for the purposes of patent procedure. The culture will be released to the public, irrevocably and without restriction to the public upon issuance of this patent. The sequence of the polynucleotide contained in the deposited material and the amino acid sequence of the polypeptide encoded thereby are controlling in the event of any conflict with the sequences provided herein. However, as will be obvious to those of skill in the art upon this disclosure, due to the degeneracy of the genetic code, polynucleotides of the present invention may comprise other nucleic acid sequences encoding the polypeptide of FIG. 1 and derivatives, variants or active fragments thereof.

Another aspect of the present invention relates to the polypeptides encoded by the polynucleotides of the present invention. In a preferred embodiment, a polypeptide of the present invention comprises the deduced amino acid sequence of human Type 2 RNase H provided in FIG. 1 as SEQ ID NO: 1. However, by "polypeptide" it is also meant to include fragments, derivatives and analogs which retain essentially the same biological activity and/or function as human Type 2 RNase H. Alternatively, polypeptides of the present invention may retain their ability to bind to an antisense-RNA duplex even though they do not function as active RNase H enzymes in other capacities. In another embodiment, polypeptides of the present invention may retain nuclease activity but without specificity for the RNA portion of an RNA/DNA duplex. Polypeptides of the present invention include recombinant polypeptides, isolated natural polypeptides and synthetic polypeptides, and fragments thereof which retain one or more of the activities described above.

In a preferred embodiment, the polypeptide is prepared recombinantly, most preferably from the culture of *E. coli* of ATCC Deposit No. 98536. Recombinant human RNase H fused to histidine codons (his-tag; in the present embodiment six histidine codons were used) expressed in *E.coli* can be conveniently purified to electrophoretic homogeneity by chromatography with Ni-NTA followed by C4 reverse phase HPLC. The purified recombinant polypeptide of SEQ ID NO: 1 is highly homologous to *E.coli* RNase H, displaying nearly 34% amino acid identity with *E.coli* RNase H1. FIG. 1 compares the protein sequences deduced from human RNase H cDNA (SEQ ID NO: 1) with those of chicken (SEQ ID NO: 2), yeast (SEQ ID NO: 3) and *E.coli* RNase HI (Gene Bank accession no. 1786408; SEQ ID NO: 4), as well as an EST deduced mouse RNase H homolog (Gene Bank accession no. AA389926 and AA518920; SEQ ID NO: 5). The deduced amino acid sequence of human RNase H (SEQ ID NO: 1) displays strong homology with yeast (21.8% amino acid identity), chicken (59%), *E.coli* RNase HI (33.6%) and the mouse EST homolog (84.3%). They are all small proteins (<40 KDa) and their estimated pIs are all 8.7 and greater. Further, the amino acid residues in *E.coli* RNase HI thought to be involved in the $Mg^{2+}$ binding site, catalytic center and substrate binding region are completely conserved in the cloned human RNase H sequence (FIG. 1).

The human Type 2 RNase H of SEQ ID NO: 1 is expressed ubiquitously. Northern blot analysis demonstrated that the transcript was abundant in all tissues and cell lines except the MCR-5 line. Northern blot analysis of total RNA from human cell lines and Poly A containing RNA from human tissues using the 1.7 kb full length probe or a 332-nucleotide probe that contained the 5' UTR and coding region of human RNase H cDNA revealed two strongly positive bands with approximately 1.2 and 5.5 kb in length and two less intense bands approximately 1.7 and 4.0 kb in length in most cell lines and tissues. Analysis with the 332-nucleotide probe showed that the 5.5 kb band contained the 5' UTR and a portion of the coding region, which suggests that this band represents a pre-processed or partially processed transcript, or possibly an alternatively spliced transcript. Intermediate sized bands may represent processing intermediates. The 1.2 kb band represents the full length transcripts. The longer transcripts may be processing intermediates or alternatively spliced transcripts.

RNase H is expressed in most cell lines tested; only MRC5, a breast cancer cell line, displayed very low levels of RNase H. However, a variety of other malignant cell lines including those of bladder (T24), breast (T-47D, HS578T), lung (A549), prostate (LNCap, DU145), and myeloid lineage (HL-60), as well as normal endothelial cells (HUVEC), expressed RNase H. Further, all normal human tissues tested expressed RNase H. Again, larger transcripts were present as well as the 1.2 kb transcript that appears to be the mature mRNA for RNase H. Normalization based on G3PDH levels showed that expression was relatively consistent in all of the tissues tested.

The Southern blot analysis of EcoRI digested human and various mammalian vertebrate and yeast genomic DNAs probed with the 1.7 kb probe shows that four EcoRI digestion products of human genomic DNA (2.4, 4.6, 6.0, 8.0 Kb) hybridized with the 1.7 kb probe. The blot re-probed with a 430 nucleotide probe corresponding to the C-terminal portion of the protein showed only one 4.6 kbp EcoRI digestion product hybridized. These data indicate that there is only one gene copy for RNase H and that the size of the gene is more than 10 kb. Both the full length and the shorter probe strongly hybridized to one EcoRI digestion product of yeast genomic DNA (about 5 kb in size), indicating a high degree of conservation. These probes also hybridized to the digestion product from monkey, but none of the other tested mammalian genomic DNAs including the mouse which is highly homologous to the human RNase H sequence.

A recombinant human RNase H (his-tag fusion protein) polypeptide of the present invention was expressed in *E.coli* and purified by Ni-NTA agarose beads followed by C4 reverse phase column chromatography. A 36 kDa protein copurified with activity measured after renaturation. The presence of the his-tag was confirmed by Western blot analyses with an anti-penta-histidine antibody (Qiagen, Germany).

Renatured recombinant human RNase H displayed RNase H activity. Incubation of 10 ng purified renatured RNase H with RNA/DNA substrate for 2 hours resulted in cleavage of 40% of the substrate. The enzyme also cleaved RNA in an oligonucleotide/RNA duplex in which the oligonucleotide was a gapmer with a 5-deoxynucleotide gap, but at a much slower rate than the full RNA/DNA substrate. This is consistent with observations with *E.coli* RNase HI (Lima, W. F. and Crooke, S. T., *Biochemistry*, 1997, 36, 390–398). It was inactive against single-stranded RNA or double-stranded RNA substrates and was inhibited by $Mn^{2+}$. The molecular weight (~36kDa) and inhibition by $Mn^{2+}$ indicate that the cloned enzyme is highly homologous to *E.coli* RNase HI and has properties consistent with those assigned to Type 2 human RNase H.

The sites of cleavage in the RNA in the full RNA/DNA substrate and the gapmer/RNA duplexes (in which the oligonucleotide gapmer had a 5-deoxynucleotide gap) resulting from the recombinant enzyme were determined. In the full RNA/DNA duplex, the principal site of cleavage was near the middle of the substrate, with evidence of less prominent cleavage sites 3' to the primary cleavage site. The primary cleavage site for the gapmer/RNA duplex was located across the nucleotide adjacent to the junction of the 2' methoxy wing and oligodeoxy nucleotide gap nearest the 3' end of the RNA. Thus, the enzyme resulted in a major cleavage site in the center of the RNA/DNA substrate and less prominent cleavages to the 3' side of the major cleavage site. The shift of its major cleavage site to the nucleotide in apposition to the DNA 2' methoxy junction of the 2' methoxy wing at the 5' end of the chimeric oligonucleotide is consistent with the observations for *E.coli* RNase HI (Crooke et al. (1995) Biochem. J. 312, 599–608; Lima, W. F. and Crooke, S. T. (1997) Biochemistry 36, 390–398). The fact that the enzyme cleaves at a single site in a 5-deoxy gap duplex indicates that the enzyme has a catalytic region of similar dimensions to that of *E.coli* RNase HI.

Accordingly, expression of large quantities of a purified human RNase H polypeptide of the present invention is useful in characterizing the activities of a mammalian form of this enzyme. In addition, the polynucleotides and polypeptides of the present invention provide a means for identifying agents which enhance the function of antisense oligonucleotides in human cells and tissues.

For example, a host cell can be genetically engineered to incorporate polynucleotides and express polypeptides of the present invention. Polynucleotides can be introduced into a host cell using any number of well known techniques such as infection, transduction, transfection or transformation. The polynucleotide can be introduced alone or in conjunction with a second polynucleotide encoding a selectable marker. In a preferred embodiment, the host comprises a mammalian cell. Such host cells can then be used not only for production of human Type 2 RNase H, but also to identify agents which increase or decrease levels of expression or activity of human Type 2 RNase H in the cell. In these assays, the host cell would be exposed to an agent suspected of altering levels of expression or activity of human Type 2 RNase in the cells. The level or activity of human Type 2 RNase in the cell would then be determined in the presence and absence of the agent. Assays to determine levels of protein in a cell are well known to those of skill in the art and include, but are not limited to, radioimmunoassays, competitive binding assays, Western blot analysis and enzyme linked immunosorbent assays (ELISAs). Methods of determining increase activity of the enzyme, and in particular increased cleavage of an antisense-mRNA duplex can be performed in accordance with the teachings of Example 5. Agents identified as inducers of the level or activity of this enzyme may be useful in enhancing the efficacy of antisense oligonucleotide therapies.

The present invention also relates to prognostic assays wherein levels of RNase in a cell type can be used in predicting the efficacy of antisense oligonucleotide therapy in specific target cells. High levels of RNase in a selected cell type are expected to correlate with higher efficacy as compared to lower amounts of RNase in a selected cell type which may result in poor cleavage of the mRNA upon binding with the antisense oligonucleotide. For example, the MRC5 breast cancer cell line displayed very low levels of RNase H as compared to other malignant cell types. Accordingly, in this cell type it may be desired to use antisense compounds which do not depend on RNase H activity for their efficacy.

Similarly, oligonucleotides can be screened to identify those which are effective antisense agents by contacting human Type 2 RNase H with an oligonucleotide and measuring binding of the oligonucleotide to the human Type 2 RNase H. Methods of determining binding of two molecules are well known in the art. For example, in one embodiment, the oligonucleotide can be radiolabeled and binding of the oligonucleotide to human Type 2 RNase H can be determined by autoradiography. Alternatively, fusion proteins of human Type 2 RNase H with glutathione-S-transferase or small peptide tags can be prepared and immobilized to a solid phase such as beads. Labeled or unlabeled oligonucleotides to be screened for binding to this enzyme can then be incubated with the solid phase. Oligonucleotides which bind to the enzyme immobilized to the solid phase can then be identified either by detection of bound label or by eluting specifically the bound oligonucleotide from the solid phase. Another method involves screening of oligonucleotide libraries for binding partners. Recombinant tagged or labeled human Type 2 RNase H is used to select oligonucleotides from the library which interact with the enzyme. Sequencing of the oligonucleotides leads to identification of those oligonucleotides which will be more effective as antisense agents.

The following nonlimiting examples are provided to further illustrate the present invention.

EXAMPLES

Example 1
Rapid Amplification of 5'-cDNA End (5'-RACE) and 3'-cDNA End (3'-RACE)

An internet search of the XREF database in the National Center of Biotechnology Information (NCBI) yielded a 361 base pair (bp) human expressed sequenced tag (EST, GenBank accession #H28861), homologous to yeast RNase H (RNH1) protein sequenced tag (EST, GenBank accession #Q04740) and its chicken homologue (accession #D26340). Three sets of oligonucleotide primers encoding the human RNase H EST sequence were synthesized. The sense primers were ACGCTGGCCGGGAGTCGAAATGCTTC (H1: SEQ ID NO: 6), CTGTTCCTGGCCCACAGAGTCGCCT-TGG (H3: SEQ ID NO: 7) and GGTCTTTCTGACCTG-GAATGAGTGCAGAG (H5: SEQ ID NO: 8). The antisense primers were CTTGCCTGGTTTCGCCCTCCGATTCT-TGT (H2: SEQ ID NO: 9), TTGATTTTCATGCCCTTCT-GAAACTTCCG (H4; SEQ ID NO: 10) and CCTCATC-CTCTATGGCAAACTTCTTAAATCTGGC (H6; SEQ ID NO: 11). The human RNase H 3' and 5' cDNAs derived from the EST sequence were amplified by polymerase chain reaction (PCR), using human liver or leukemia (lymphoblastic Molt-4) cell line Marathon ready cDNA as templates, H1 or H3/AP1 as well as H4 or H6/AP2 as primers (Clontech, Palo Alto, Calif.). The fragments were subjected to agarose gel electrophoresis and transferred to nitrocellulose membrane (Bio-Rad, Hercules Calif.) for confirmation by Southern blot, using $^{32}$P-labeled H2 and H1 probes (for 3' and 5' RACE products, respectively, in accordance with procedures described by Ausubel et al., Current Protocols in Molecular Biology, Wiley and Sons, New York, N.Y., 1988. The confirmed fragments were excised from the agarose gel and purified by gel extraction (Qiagen, Germany), then subcloned into Zero-blunt vector (Invitrogen, Carlsbad, Calif.) and subjected to DNA sequencing.

Example 2
Screening of the cDNA Library, DNA Sequencing and Sequence Analysis A human liver cDNA lambda phage Uni-ZAP library (Stratagene, La Jolla, Calif.) was screened using the RACE products as specific probes. The positive cDNA clones were excised into the pBluescript phagemid (Stratagene, La Jolla Calif.) from lambda phage and subjected to DNA sequencing with an automatic DNA sequencer (Applied Biosystems, Foster City, Calif.) by Retrogen Inc. (San Diego, Calif.). The overlapping sequences were aligned and combined by the assembling programs of MacDNASIS v3.0 (Hitachi Software Engineering America, South San Francisco, Calif.). Protein structure and subsequence analysis were performed by the program of MacVector 6.0 (Oxford Molecular Group Inc., Campbell, Calif.). A homology search was performed on the NCBI database by internet E-mail.

Example 3
Northern Blot and Southern Blot Analysis

Total RNA from different human cell lines (ATCC, Rockville, Md.) was prepared and subjected to formaldehyde agarose gel electrophoresis in accordance with procedures described by Ausubel et al., Current Protocols in Molecular Biology, Wiley and Sons, New York, N.Y., 1988, and transferred to nitrocellulose membrane (Bio-Rad, Hercules Calif.). Northern blot hybridization was carried out in QuickHyb buffer (Stratagene, La Jolla, Calif.) with 32P-labeled probe of full length RNase H cDNA clone or primer H1/H2 PCR-generated 322-base N-terminal RNase H cDNA fragment at 68° C. for 2 hours. The membranes were washed twice with 0.1% SSC/0.1% SDS for 30 minutes and subjected to auto-radiography. Southern blot analysis was carried out in 1x pre-hybridization/hybridization buffer (BRL, Gaithersburg, Md.) with a $^{32}$P-labeled 430 bp C-terminal restriction enzyme PstI/PvuII fragment or 1.7 kb full length cDNA probe at 60° C. for 18 hours. The membranes were washed twice with 0.1% SSC/0.1% SDS at 60° C. for 30 minutes, and subjected to autoradiography.

Example 4
Expression and Purification of the Cloned RNase Protein

The cDNA fragment coding the full RNase H protein sequence was amplified by PCR using 2 primers, one of which contains restriction enzyme NdeI site adapter and six histidine (his-tag) codons and 22 bp protein N terminal coding sequence. The fragment was cloned into expression vector pET17b (Novagen, Madison, Wis.) and confirmed by DNA sequencing. The plasmid was transfected into E.coli BL21(DE3) (Novagen, Madison, Wis.). The bacteria were grown in M9ZB medium at 32° C. and harvested when the $OD_{600}$ of the culture reached 0.8, in accordance with procedures described by Ausubel et al., Current Protocols in Molecular Biology, Wiley and Sons, New York, N.Y., 1988. Cells were lysed in 8M urea solution and recombinant protein was partially purified with Ni-NTA agarose (Qiagen, Germany). Further purification was performed with C4 reverse phase chromatography (Beckman, System Gold, Fullerton, Calif.) with 0.1% TFA water and 0.1% TFA acetonitrile gradient of 0% to 80% in 40 minutes as described by Deutscher, M. P., Guide to Protein Purification, Methods in Enzymology 182, Academic Press, New York, N.Y., 1990. The recombinant proteins and control samples were collected, lyophilized and subjected to 12% SDS-PAGE as described by Ausubel et al. (1988) Current Protocols in Molecular Biology, Wiley and Sons, New York, N.Y. The purified protein and control samples were resuspended in 6 M urea solution containing 20 mM Tris HCl, pH 7.4, 400 mM NaCl, 20% glycerol, 0.2 mM PMSF, 5 mM DTT, 10 μg/ml aprotinin and leupeptin, and refolded by dialysis with decreasing urea concentration from 6 M to 0.5 M as well as DTT concentration from 5 mM to 0.5 mM as described by Deutscher, M. P., Guide to Protein Purification, Methods in Enzymology 182, Academic Press, New York, N.Y., 1990. The refolded proteins were concentrated (10 fold) by Centricon (Amicon, Danvers, Mass.) and subjected to RNase H activity assay.

Example 5
RNase H Activity Assay $^{32}$P-end-labeled 17-mer RNA, GGGCGCCGTCGGT-GTGG (SEQ ID NO: 12) described by Lima, W. F. and Crooke, S. T., Biochemistry, 1997 36, 390–398, was gel-purified as described by Ausubel et al., Current Protocols in Molecular Biology, Wiley and Sons, New York, N.Y., 1988 and annealed with a tenfold excess of its complementary 17-mer oligodeoxynucleotide or a 5-base DNA gapmer, i.e., a 17mer oligonucleotide which has a central portion of 5 deoxynucleotides (the "gap") flanked on both sides by 6 2'-methoxynucleotides. Annealing was done in 10 mM Tris HCl, pH 8.0, 10 mM MgCl, 50 mM KCl and 0.1 mM DTT to form one of three different substrates: (a) single strand (ss) RNA probe, (b) full RNA/DNA duplex and (c) RNA/DNA gapmer duplex. Each of these substrates was incubated with protein samples at 37° C. for 5 minutes to 2 hours at the same conditions used in the annealing procedure and the reactions were terminated by adding EDTA in accordance with procedures described by Lima, W. F. and Crooke, S. T., *Biochemistry*, 1997, 36, 390–398. The reaction mixtures were precipitated with TCA centrifugation and the supernatant was measured by liquid scintillation counting (Beckman LS6000IC, Fullerton, Calif.). An aliquot of the reaction mixture was also subjected to denaturing (8 M urea) acrylamide gel electrophoresis in accordance with procedures described by Lima, W. F. and Crooke, S. T., *Biochemistry*, 1997, 36, 390–398 and Ausubel et al., *Current Protocols in Molecular Biology*, Wiley and Sons, New York, N.Y., 1988.

What is claimed is:

1. A nucleic acid probe at least 13 nucleobases in length, and complementary to a portion of a nucleic acid encoding a human Type 2 RNase H polypeptide having SEQ ID NO: 1.

* * * * *

```
                           SEQUENCE LISTING

<160> NUMBER OF SEQ ID NOS: 12

<210> SEQ ID NO 1
<211> LENGTH: 286
<212> TYPE: PRT
<213> ORGANISM: Homo sapiens

<400> SEQUENCE: 1

Met Ser Trp Leu Leu Phe Leu Ala His Arg Val Ala Leu Ala Ala Leu
 1               5                  10                  15

Pro Cys Arg Arg Gly Ser Arg Gly Phe Gly Met Phe Tyr Ala Val Arg
            20                  25                  30

Arg Gly Arg Lys Thr Gly Val Phe Leu Thr Trp Asn Glu Cys Arg Ala
        35                  40                  45

Gln Val Asp Arg Phe Pro Ala Ala Arg Phe Lys Lys Phe Ala Thr Glu
    50                  55                  60

Asp Glu Ala Trp Ala Phe Val Arg Lys Ser Ala Ser Pro Glu Val Ser
65                  70                  75                  80

Glu Gly His Glu Asn Gln His Gly Gln Glu Ser Glu Ala Lys Pro Gly
                85                  90                  95

Lys Arg Leu Arg Glu Pro Leu Asp Gly Asp Gly His Glu Ser Ala Gln
            100                 105                 110

Pro Tyr Ala Lys His Met Lys Pro Ser Val Glu Pro Ala Pro Pro Val
        115                 120                 125

Ser Arg Asp Thr Phe Ser Tyr Met Gly Asp Phe Val Val Val Tyr Thr
    130                 135                 140

Asp Gly Cys Cys Ser Ser Asn Gly Arg Arg Lys Pro Arg Ala Gly Ile
145                 150                 155                 160

Gly Val Tyr Trp Gly Pro Gly His Pro Leu Asn Val Gly Ile Arg Leu
                165                 170                 175

Pro Gly Arg Gln Thr Asn Gln Arg Ala Glu Ile His Ala Ala Cys Lys
            180                 185                 190

Ala Ile Glu Gln Ala Lys Thr Gln Asn Ile Asn Lys Leu Val Leu Tyr
        195                 200                 205

Thr Asp Ser Met Phe Thr Ile Asn Gly Ile Thr Asn Trp Val Gln Gly
    210                 215                 220

Trp Lys Lys Asn Gly Trp Lys Thr Ser Ala Gly Lys Glu Val Ile Asn
225                 230                 235                 240

Lys Glu Asp Phe Val Ala Leu Glu Arg Leu Thr Gln Gly Met Asp Ile
                245                 250                 255

Gln Trp Met His Val Pro Gly His Ser Gly Phe Ile Gly Asn Glu Glu
            260                 265                 270

Ala Asp Arg Leu Ala Arg Glu Gly Ala Lys Gln Ser Glu Asp
        275                 280                 285

<210> SEQ ID NO 2
<211> LENGTH: 293
<212> TYPE: PRT
<213> ORGANISM: Gallus sp.
```

```
<400> SEQUENCE: 2

Met Leu Arg Trp Leu Val Ala Leu Leu Ser His Ser Cys Phe Val Ser
  1               5                  10                  15

Lys Gly Gly Gly Met Phe Tyr Ala Val Arg Lys Gly Arg Gln Thr Gly
                 20                  25                  30

Val Tyr Arg Thr Trp Ala Glu Cys Gln Gln Gln Val Asn Arg Phe Pro
             35                  40                  45

Ser Ala Ser Phe Lys Lys Phe Ala Thr Glu Lys Glu Ala Trp Ala Phe
         50                  55                  60

Val Gly Ala Gly Pro Pro Asp Gly Gln Gln Ser Ala Pro Ala Glu Thr
 65                  70                  75                  80

His Gly Ala Ser Ala Val Ala Gln Glu Asn Ala Ser His Arg Glu Glu
                 85                  90                  95

Pro Glu Thr Asp Val Leu Cys Cys Asn Ala Cys Lys Arg Arg Tyr Glu
                100                 105                 110

Gln Ser Thr Asn Glu Glu His Thr Val Arg Arg Ala Lys His Asp Glu
                115                 120                 125

Glu Gln Ser Thr Pro Val Val Ser Glu Ala Lys Phe Ser Tyr Met Gly
            130                 135                 140

Glu Phe Ala Val Val Tyr Thr Asp Gly Cys Cys Ser Gly Asn Gly Arg
145                 150                 155                 160

Asn Arg Ala Arg Ala Gly Ile Gly Val Tyr Trp Gly Pro Gly His Pro
                165                 170                 175

Leu Asn Ile Ser Glu Arg Leu Pro Gly Arg Gln Thr Asn Gln Arg Ala
                180                 185                 190

Glu Ile His Ala Ala Cys Lys Ala Ile Glu Gln Ala Lys Ser Gln Asn
                195                 200                 205

Ile Lys Lys Leu Ile Ile Tyr Thr Asp Ser Lys Phe Thr Ile Asn Gly
210                 215                 220

Ile Thr Ser Trp Val Glu Asn Trp Lys Thr Asn Gly Trp Arg Thr Ser
225                 230                 235                 240

Ser Gly Gly Ser Val Ile Asn Lys Glu Asp Phe Gln Lys Leu Asp Ser
                245                 250                 255

Leu Ser Lys Gly Ile Glu Ile Gln Trp Met His Ile Pro Gly His Ala
                260                 265                 270

Gly Phe Gln Gly Asn Glu Glu Ala Asp Arg Leu Ala Arg Glu Gly Ala
                275                 280                 285

Ser Lys Gln Lys Leu
                290

<210> SEQ ID NO 3
<211> LENGTH: 348
<212> TYPE: PRT
<213> ORGANISM: Saccharomyces sp.

<400> SEQUENCE: 3

Met Ala Arg Gln Gly Asn Phe Tyr Ala Val Arg Lys Gly Arg Glu Thr
  1               5                  10                  15

Gly Ile Tyr Asn Thr Trp Asn Glu Cys Lys Asn Gln Val Asp Gly Tyr
                 20                  25                  30

Gly Gly Ala Ile Tyr Lys Lys Phe Asn Ser Tyr Glu Gln Ala Lys Ser
             35                  40                  45

Phe Leu Gly Gln Pro Asn Thr Ser Asn Tyr Gly Ser Ser Thr His
         50                  55                  60
```

```
Ala Gly Gly Gln Val Ser Lys Pro His Thr Thr Gln Lys Arg Val His
 65                  70                  75                  80

Arg Arg Asn Arg Pro Leu His Tyr Ser Ser Leu Thr Ser Ser Ala
                 85                  90                  95

Cys Ser Ser Leu Ser Ser Ala Asn Thr Asn Thr Phe Tyr Ser Val Lys
                100                 105                 110

Ser Asn Val Pro Asn Ile Glu Ser Lys Ile Phe Asn Asn Trp Lys Asp
            115                 120                 125

Cys Gln Ala Tyr Val Lys His Lys Arg Gly Ile Thr Phe Lys Lys Phe
        130                 135                 140

Glu Asp Gln Leu Ala Ala Glu Asn Phe Ile Ser Gly Met Ser Ala His
145                 150                 155                 160

Asp Tyr Lys Leu Met Asn Ile Ser Lys Glu Ser Phe Glu Ser Lys Tyr
                165                 170                 175

Lys Leu Ser Ser Asn Thr Met Tyr Asn Lys Ser Met Asn Val Tyr Cys
            180                 185                 190

Asp Gly Ser Ser Phe Gly Asn Gly Thr Ser Ser Ser Arg Ala Gly Tyr
        195                 200                 205

Gly Ala Tyr Phe Glu Gly Ala Pro Glu Glu Asn Ile Ser Glu Pro Leu
    210                 215                 220

Leu Ser Gly Ala Gln Thr Asn Asn Arg Ala Glu Ile Glu Ala Val Ser
225                 230                 235                 240

Glu Ala Leu Lys Lys Ile Trp Glu Lys Leu Thr Asn Glu Lys Glu Lys
                245                 250                 255

Val Asn Tyr Gln Ile Lys Thr Asp Ser Glu Tyr Val Thr Lys Leu Leu
            260                 265                 270

Asn Asp Arg Tyr Met Thr Tyr Asp Asn Lys Lys Leu Glu Gly Leu Pro
        275                 280                 285

Asn Ser Asp Leu Ile Val Pro Leu Val Gln Arg Phe Val Lys Val Lys
    290                 295                 300

Lys Tyr Tyr Glu Leu Asn Lys Glu Cys Phe Lys Asn Asn Gly Lys Phe
305                 310                 315                 320

Gln Ile Glu Trp Val Lys Gly His Asp Gly Asp Pro Gly Asn Glu Met
                325                 330                 335

Ala Asp Phe Leu Ala Lys Lys Gly Ala Ser Arg Arg
            340                 345

<210> SEQ ID NO 4
<211> LENGTH: 155
<212> TYPE: PRT
<213> ORGANISM: Escherichia coli

<400> SEQUENCE: 4

Met Leu Lys Gln Val Glu Ile Phe Thr Asp Gly Ser Cys Leu Gly Asn
  1               5                  10                  15

Pro Gly Pro Gly Gly Tyr Gly Ala Ile Leu Arg Tyr Arg Gly Arg Glu
                 20                  25                  30

Lys Thr Phe Ser Ala Gly Tyr Thr Arg Thr Thr Asn Asn Arg Met Glu
             35                  40                  45

Leu Met Ala Ala Ile Val Ala Leu Glu Ala Leu Lys Glu His Cys Glu
         50                  55                  60

Val Ile Leu Ser Thr Asp Ser Gln Tyr Val Arg Gln Gly Ile Thr Gln
 65                  70                  75                  80

Trp Ile His Asn Trp Lys Lys Arg Gly Trp Lys Thr Ala Asp Lys Lys
                 85                  90                  95
```

```
Pro Val Lys Asn Val Asp Leu Trp Gln Arg Leu Asp Ala Ala Leu Gly
            100                 105                 110

Gln His Gln Ile Lys Trp Glu Trp Val Lys Gly His Ala Gly His Pro
        115                 120                 125

Glu Asn Glu Arg Cys Asp Glu Leu Ala Arg Ala Ala Met Asn Pro
130                 135                 140

Thr Leu Glu Asp Thr Gly Tyr Gln Val Glu Val
145                 150                 155

<210> SEQ ID NO 5
<211> LENGTH: 216
<212> TYPE: PRT
<213> ORGANISM: Mus musculus

<400> SEQUENCE: 5

Gly Ile Cys Gly Leu Gly Met Phe Tyr Ala Val Arg Arg Gly Arg Arg
  1               5                  10                  15

Pro Gly Val Phe Leu Ser Trp Ser Glu Cys Lys Ala Gln Val Asp Arg
             20                  25                  30

Phe Pro Ala Ala Arg Phe Lys Lys Phe Ala Thr Glu Asp Glu Ala Trp
         35                  40                  45

Ala Phe Val Arg Ser Ser Ser Pro Asp Gly Ser Lys Gly Gln Glu
50                  55                  60

Ser Ala His Glu Gln Lys Ser Gln Ala Lys Thr Ser Lys Arg Pro Arg
65                  70                  75                  80

Glu Pro Leu Val Val Val Tyr Thr Asp Gly Cys Cys Ser Ser Asn Gly
                 85                  90                  95

Arg Lys Arg Ala Arg Ala Gly Ile Gly Val Tyr Trp Gly Pro His His
            100                 105                 110

Pro Leu Asn Val Arg Ile Arg Leu Pro Gly Arg Gln Thr Asn Gln Arg
        115                 120                 125

Ala Glu Ile His Ala Ala Cys Lys Ala Val Met Gln Ala Lys Ala Gln
130                 135                 140

Asn Ile Ser Lys Leu Val Leu Tyr Thr Asp Ser Met Phe Thr Ile Asn
145                 150                 155                 160

Gly Ile Thr Asn Trp Val Gln Gly Trp Lys Lys Asn Gly Trp Arg Thr
                165                 170                 175

Ser Thr Gly Lys Asp Val Ile Asn Lys Glu Asp Phe Met Glu Leu Asp
            180                 185                 190

Glu Leu Thr Gln Gly Met Asp Ile Gln Trp Met His Ile Pro Gly His
        195                 200                 205

Ser Gly Phe Val Gly Asn Glu Glu
    210                 215

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:Synthetic

<400> SEQUENCE: 6
acgctggccg ggagtcgaaa tgcttc                                        26

<210> SEQ ID NO 7
<211> LENGTH: 28
<212> TYPE: DNA
```

```
<213> ORGANISM: Artificial Sequence
<220> FEATURE:
<223> OTHER INFORMATION: Description of Artificial Sequence:Synthetic

<400> SEQUENCE: 7
ctgttcctgg cccacagagt cgccttgg                                             28

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:Synthetic

<400> SEQUENCE: 8
ggtctttctg acctggaatg agtgcagag                                            29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Synthetic

<400> SEQUENCE: 9
cttgcctggt ttcgccctcc gattcttgt                                            29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:Synthetic

<400> SEQUENCE: 10
ttgattttca tgccttctg aaacttccg                                             29

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:Synthetic

<400> SEQUENCE: 11
cctcatcctc tatggcaaac ttcttaaatc tggc                                      34

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:Synthetic

<400> SEQUENCE: 12
gggcgccgtc ggtgtgg                                                         17
```